United States Patent [19]

Spector et al.

[11] Patent Number: 4,555,537
[45] Date of Patent: Nov. 26, 1985

[54] HETERO NITROGEN CONTAINING COMPOUNDS AND POLYMERMS LIGHT STABILIZED WITH SAID COMPOUNDS

[75] Inventors: Richard Spector, Kendall Park; Donald R. Maulding, Somerville, both of N.J.

[73] Assignee: American Cyanamid Company, Stamford, Conn.

[21] Appl. No.: 520,933

[22] Filed: Aug. 8, 1983

[51] Int. Cl.⁴ .................................... C08K 5/34
[52] U.S. Cl. ...................... 524/97; 524/105; 524/106; 544/139; 546/210; 548/300
[58] Field of Search .............. 524/97, 105, 106; 544/139; 546/210; 548/300

[56] References Cited

U.S. PATENT DOCUMENTS

| 2,576,306 | 11/1951 | Morey | 548/300 |
| 3,448,074 | 6/1969 | Kitaoka et al. | 524/105 |
| 3,645,965 | 2/1972 | Murayama et al. | 524/105 |
| 3,971,757 | 7/1976 | Rasberger | 524/106 |

OTHER PUBLICATIONS

Kena et al, J.A.C.S., vol. 100, No. 3, 1978, pp. 934–937.

*Primary Examiner*—Lester L. Lee
*Attorney, Agent, or Firm*—John W. Cornell; Henry C. Jeanette; Steven J. Hultquist

[57] ABSTRACT

Compounds of the formula:

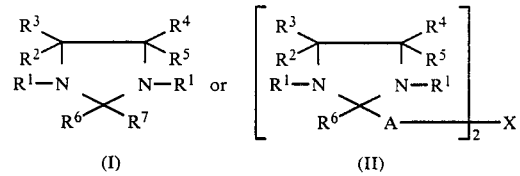

are disclosed as light stabilizers for polymers normally subject to degradation by light.

21 Claims, No Drawings

HETERO NITROGEN CONTAINING COMPOUNDS AND POLYMERMS LIGHT STABILIZED WITH SAID COMPOUNDS

This invention relates to certain novel compounds and to their use as stabilizers for polymers normally subject to degradation by light and/or ultraviolet (actinic) radiation. More particularly, this invention relates to novel compounds of the formula:

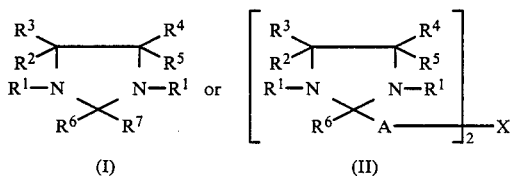

wherein:
(1) $R^1$ represents hydrogen, alkyl ($C_1$–$C_6$) hydroxyl, or oxyl;
(2) $R^2$ and $R^3$, which may be the same or different, represent alkyl ($C_1$–$C_6$), cycloalkyl ($C_5$–$C_6$), or together with the carbon to which they are attached form a cycloalkyl ($C_5$–$C_6$) radical;
(3) $R^4$ and $R^5$, which may be the same or different, represent the same groups as $R^2$ and $R^3$,
(4) $R^6$ and $R^7$, which may be the same or different, represent alkyl ($C_1$–$C_{18}$), substituted alkyl ($C_1$–$C_8$), or together with the carbon to which they are attached form a cycloalkyl ($C_5$–$C_6$) radical optionally substituted with alkyl ($C_1$–$C_8$), or substituted cycloalkyl ($C_5$–$C_6$) radical, or a substituted or unsubstituted alkyl ($C_1$–$C_8$)-substituted cycloalkyl ($C_5$–$C_6$) radical, wherein said substituents are selected from amino, cyano, hydroxyl,

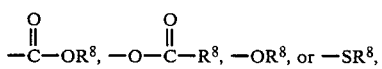

wherein $R^8$ is selected from alkyl ($C_1$–$C_{18}$) and cycloakllyl ($C_5$–$C_6$),

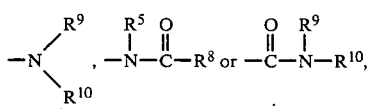

wherein $R^9$ is hydrogen, alkyl ($C_1$–$C_{18}$), or cycloalkyl ($C_5$–$C_6$), $R^{10}$ is alkyl ($C_1$–$C_{18}$) or cycloalkyl ($C_5$–$C_6$), or $R^9$ and $R^{10}$, together with the nitrogen atom to which they are attached, form a ring represented by the formula:

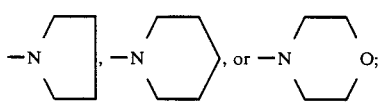

(5) the group

represents alkylene ($C_1$–$C_6$), arylene ($C_6$–$C_{10}$), arylenedialkyl ($C_8$–$C_{12}$), or an X-substituted alkylene ($C_1$–$C_8$), or A together with $R^6$ and the carbon atom to which they are attached form an X-substituted cycloalkyl ring ($C_5$–$C_6$), wherein X represents:

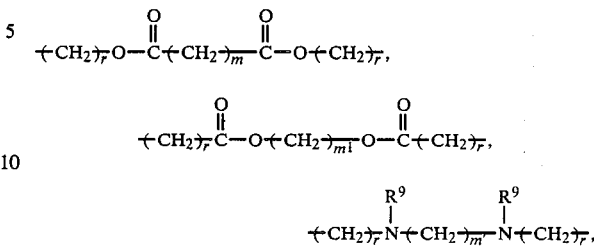

wherein m is zero to 6, m' is 2 to 6, and r is zero to 2.

In the preferred embodiment, the compounds of formulas (I) and (II) are represented by formulas (III) and (IV), respectively.

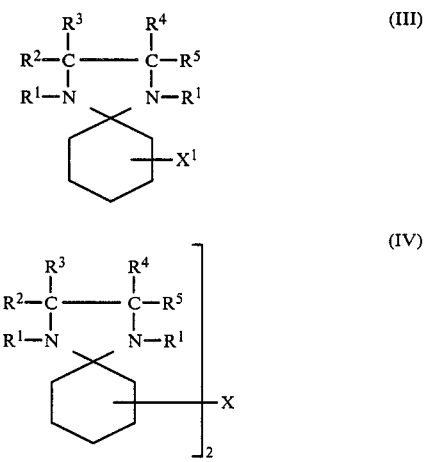

wherein the substituent $X^1$ in compound (III) is hydrogen, alkyl ($C_1$–$C_{18}$) or as defined previously for substituents in (4) above, and the substituent X in compound (IV) is as defined previously in (5) above.

In the especially preferred embodiments, the compounds of (III) and (IV) are those wherein $R^1$ is hydrogen and $R^2$–$R^5$ are all methyl.

It is well-known that sunlight and other sources of ultraviolet radiation cause degradation of polyolefins as evidenced by embrittlement or yellowing of plastic articles made therefrom. It is also well-known that this degradation can be inhibited by use of ultraviolet light stabilizers incorporated in or on such articles. Various additives, used alone or in combinations, have been suggested to inhibit such light degradation in order to prolong the useful lives of articles made from polyolefins. Since none has been found to be completely satisfactory, research continues in order to find compounds or combinations of compounds which will be more satisfactory. The present invention arose out of such research and resulted in the discovery of novel compounds which stabilize polymers against degradation by ultraviolet light.

In accordance with the present invention, it has been discovered that the above-described compounds of formulas (I) and (II) provide effective stabilization of polymers, particularly polyolefins, against deterioration by light, particularly ultraviolet light, when incorporated in said polymers in effective amounts.

Also in accordance with the present invention, compositions of matter stabilized against deterioration by light are provided by incorporating compounds of formulas (I) and (II) into said polymers.

The compounds of formula (I) may be prepared by the reaction of a suitable diamine and monoketone, preferably a cyclohexanone, as disclosed by Keana et al., J. Am. Chem. Soc. 1978, 100 (3), pgs. 934–937, and Bergmann in U.S. Pat. No. 2,525,855.

Suitable diamines which may be used in this reaction include 2,3-diamino-2,3-dimethylbutane; 2,3-diamino-2,3-diethylbutane; 2,3-diamino-2,3-dicyclohexylbutane; and the like.

Suitable ketones which may be used include the following:
acetone,
2-butanone,
2-pentanone,
4-heptanone,
2-octanone,
5-cyano-2-pentanone,
1-cyano-3-pentanone,
5-hydroxy-2-pentanone,
1-hydroxy-2-pentanone,
ethyl 4-acetylbutyrate,
cyclohexyl 4-acetylbutyrate
ethyl acetoacetate,
cyclohexyl acetoacetate,
ethyl butyrylacetate,
cyclohexanone,
2-methylcyclohexanone,
2-isopropylcyclohexanone,
4-tert.-butylcyclohexanone,
4-nonylcyclohexanone,
3-pentadecylcyclohexanone,
4-octadecylcyclohexanone
3-octadecylcyclohexanone,
3-methoxycyclohexanone,
3-butoxycyclohexanone,
3-octyloxycyclohexanone,
3-dodecylthiocyclohexanone,
3-(heptadecyloxymethyl)cyclohexanone,
4-(2-cyanoethyl)cyclohexanone,
2,2,6,6-tetrakis(2-cyanoethyl)cyclohexanone,
4-hydroxycyclohexanone,
3-cyanocyclohexanone,
4-(decanoyloxy)cyclohexanone,
3-(dicyclohexylamino)cyclohexanone,
3-(2-hydroxyethyl)cyclohexanone,
2-(ethoxymethylene)cyclohexanone,
2-(2-ethoxyethyl)cyclohexanone,
2-(3-octyloxypropyl)cyclohexanone,
3-[[hexadecycloxy)carbonyl]methyl]cyclohexanone,
3-[bis[(hexadecycloxy)carbonyl]methyl]cyclohexanone,
3-[[(methoxy)carbonyl]methyl]cyclohexanone,
3-[[(cyclohexyloxy)carbonyl]methyl]cyclohexanone,
4-[6-[(ethoxy)carbonyl]hexyl]cyclohexanone,
4-(dodecylamino)cyclohexanone,
4-(didodecylamino)cyclohexanone,
4-(octadecylamino)cyclohexanone,
3-(1-pyrrolidinyl)cyclohexanone,
3-(1-piperidinyl)cyclohexanone,
3-(4-morpholinyl)cyclohexanone,
4-acetamidocyclohexanone,
3-N-methylacetamidocyclohexanone,
3-dodecanoylaminocyclohexanone,
4-octadecanoylaminocyclohexanone, and the like.

The compounds of formula (I) wherein $R^1$ is alkyl may be prepared by alkylating the corresponding compound wherein $R^1$ is hydrogen.

The compounds of formula (I) wherein $R^1$ is hydroxyl or oxyl may be prepared by reacting the corresponding compound wherein $R^1$ is hydrogen with m-chloroperoxybenzoic acid to form the nitroxide and reducing this to the N-hydroxy-substituted compound, as disclosed by Keana et al. The compounds of formula (I) wherein $R^1$ is hydroxyalkyl may be prepared by reacting the corresponding compound of formula (I) wherein $R^1$ is hydrogen with a suitable epoxide.

Suitable diketones which may be used to prepare some of the compounds of formula (II) include the following:
2,5-hexanedione,
2,9-decanedione,
4,4'-methylenebis(cyclohexanone),
4,4'-hexamethylenebis(cyclohexanone),
1,4-diacetylbenzene,
1,4-bis(acetylmethyl)benzene, and the like.

The other compounds of formula (II) may be prepared by reacting a suitable diamine with an appropriate ketone to prepare an intermediate compound of formula (I) containing a hydroxyl, carboxyl, carbalkoxy, or halo substituent, and further reacting the intermediate with a suitable dicarboxylic acid, diol, or alkylenediamine. Suitable intermediate compounds of formula (I) include the following:
2-(3-choropropyl)-2,4,4,5,5-pentamethylimidazolidine,
2-(3-hydroxypropyl)-2,4,4,5,5-pentamethylimidazolidine,
2-(ethoxycarbonyl)methyl-2,4,4,5,5-pentamethylimidazolidine,
8-chloro-2,2,3,3-tetramethyl-1,4-diazaspiro-[4.5]decane,
8-hydroxy-2,2,3,3-tetramethyl-1,4-diazaspiro-[4.5] decane,
7-(ethoxycarbonyl)methyl-2,2,3,3-tetramethyl-1,4-diazaspiro[4.5]decane,
8-(2-carboxyethyl)-2,2,3,3-tetramethyl-1,4-diazaspiro[4.5]decane,
and the like.

Suitable dicarboxylic acids, diols, and alkylenediamines which may be reacted with the intermediate compound include the following: oxalic, malonic, succinic, glutamic acids, and the like;
1,2-ethanediol; 1,3-propanediol; 1,4-butanediol; 2,3-butanediol; 1,6-hexanediol; 1,4-cyclohexanediol; 1,3-cyclopentanediol, and the like;
1,2-diaminoethane; 1,4-diaminobutane, 1,6-diaminohexane, N,N'-dimethyl-1,4-diaminobutane, N,N'-dicyclopentyl-1,6-diaminohexane, and the like.

Illustrative examples of the compounds of formula (I) include the following:
2,2,3,3-tetramethyl-1,4-diazaspiro[4.5]decane,
1,2,2,3,3,4-hexamethyl-1,4-diazaspiro[4.5]decane,
1,4-dibutyl-2,2,3,3-tetramethyl-1,4-diazaspiro[4.5]decane,
1-hydroxy-2,2,3,3-tetramethyl-1,4-diazaspiro[4.5]decane,
2,2,3,3-tetramethyl-1,4-diazaspiro[4.5]dec-1-yloxy,
2,2,3,3-tetramethyl-1,4-diazaspiro[4.5]decane-1,4-diylbisoxy,
4-hydroxy-2,2,3,3-tetramethyl-1,4-diazaspiro[4.5]dec-1-yloxy,
2,2,3,3-tetrabutyl-14,diazaspiro[4.5]decane,
2,2,3,3-tetrahexyl-1,4-diazaspiro[4.5]decane,
2,2,3,3-tetramethyl-8-nonyl-1,4-diazaspiro[4.5]decane, 2,2,3,3-tetramethyl-8-octadecyl-1,4-diazaspiro[4.5]decane,
2,2,3,3-tetramethyl-7-octadecyl-1,4-diazaspiro[4.5]decane,
7-butoxy-2,2,3,3-tetramethyl-1,4-diazaspiro[4.5]decane,
7-octyloxy-2,2,3,3-tetramethyl-1,4-diazaspiro[4.5]decane,
7-dodecylthio-2,2,3,3-tetramethyl-1,4-diazaspiro[4.5]decane,
2,2,3,3tetramethyl-7-octadecylthio-1,4-diazaspiro[4.5]decane,
6,6,10,10-tetrakis(2-cyanoethyl)-2.2.3.3-tetramethyl-1.4-diazaspiro[4.5]decane,
8-hydroxy-2,2,3,3-tetramethyl-1,4-diazaspiro[4.5]decane,
8-cyano-2,2,3,3-tetramethyl-1,4-diazaspiro[4.5]decane,
8-amino-2,2,3,3-tetramethyl-1,4-diazaspiro[4.5]decane,
7-dicyclohexylamino-2,2,3,3-tetramethyl-1,4-diazaspiro[4.5]decane,
7-dodecylamino-2,2,3,3-tetramethyl-1,4-diazaspiro[4.5]decane,
2,2,3,3-tetramethyl-7-(1-pyrrolidinyl)-1,4-diazaspiro[4.5]decane,
2,2,3,3-tetramethyl-7-(1-piperidinyl)-1,4-diazaspiro[4.5]decane,
2,2,3,3-tetramethyl-7-(4-morpholinyl-1,4-diazaspiro[4.5]decane,
2,2,3,3-tetramethyl-8-(decanoyloxy)-1,4-diazaspiro[4.5]decane,
2,2,3,3-tetramethyl-8-(dodecylamino)-1,4-diazaspiro[4.5]decane,
2,2,3,3-tetramethyl-8-(octadecylamino)-1,4-diazaspiro[4.5]decane,
7-[[(hexadecycloxy)carbonyl]methyl]-2,2,3,3-tetramethyl-1,4-diazaspiro[4.5]decane,
7-[[(octadecylamino)carbonyl]ethyl]-2,2,3,3-tetramethyl-1,4-diazaspiro[4.5]decane,
7-[bis[(hexadecycloxy)carbonyl]methyl]-2,2,3,3-tetramethyl-1,4-diazaspiro[4.5]decane,
7-[bis[(octadecylamino)carbonyl]methyl]-2,2,3,3-tetramethyl-1,4-diazaspiro[4.5]decane,
2,2,4,4,5,5-hexamethylimidazolidine,
2-n-hexyl-2,4,4,5,5-pentamethylimidazolidine,
2,4,4,5,5-pentamethyl-2-n-octadecylimidazolidine,
1,2,2,3,4,4,5,5-octamethylimidazolidine,
1-hydroxy-2,4,4,5,5-pentamethyl-2-nonylimidazolidine,
4,4,5,5-tetramethyl-2,2-dipropylimidazolidine,
1-hydroxy-2,4,4,5,5-pentamethyl-2-n-octadecylimidazolidine,
1-hydroxy-2,4,4,5,5-pentamethyl-2-n-octadecyl-3-oxyimidazolidine,
2,4,4,5,5-pentamethyl-2-n-octadecyl-1,3-dioxyimidazolidine,
2-(2-cyanoethyl)-2,4,4,5,5-pentamethylimidazolidine,
2-(2-hydroxyethyl)-2,4,4,5,5-pentamethylimidazolidine,
2-(2-aminoethyl)-2,4,4,5,5-pentamethylimidazolidine,
2-(2-ethylaminoethyl)-2,4,4,5,5-pentamethylimidazolidine,
2-[(octadecylamino)carbonyl]ethyl-2,4,4,5,5-pentamethylimidazolidine,
2-[(hexadecycloxycarbonyl]methyl-2,4,4,5,5-pentamethylimidazolidine,
and the like.

Illustrative examples of the compounds of formula (II) include the following:
8,8'-hexamethylenebis(2,2,3,3-tetraethyl-1,4-diazaspiro[4.5]decane),
8,8'-[tetramethylenebis(carbonyloxy)]bis(2,2,3,3-tetramethyl-1,4-diazaspiro[4.5]decane),
7,7'-[hexamethylenebis(oxycarbonylmethyl)]bis(2,2,3,3-tetramethyl-1,4-diazaspiro[4.5]decane),
8,8'-methylenebis(2,2,3,3-tetraethyl-1,4-diazaspiro[4.5]decane),
8,8'-[tetramethylenebis(amino)]bis(2,2,3,3-tetramethyl-1,4-diazaspiro[4.5]decane),
8,8'-[hexamethylenebis(amino)]bis(2,2,3,3-tetramethyl-1,4-diazaspiro[4.5]decane),
2,2'-ethylenebis(2,4,4,5,5-pentamethylimidazolidine),
2,2'-hexamethylenebis(2,4,4,5,5-pentamethylimidazolidine),
2,2'-[tetramethylenebis(oxycarbonylethyl)]bis(2,4,4,5,5-pentamethylimidazolidine),
2,2'-[ethylenebis(oxycarbonylmethyl)]bis(2,4,4,5,5-pentamethylimidazolidine),
2,2'-[tetramethylenebis(aminomethyl)]bis(2,4,4,5,5-pentamethylimidazolidine),
2,2'-[tetramethylenebis(carbonyloxymethyl)]bis(2,4,4,5,5-pentamethylimidazolidine),
and the like.

Polymeric materials susceptible to degradation by light include natural and synthetic polymers such as natural and synthetic rubbers and homo-, co-, and ter-polymers of acrylonitrile, butadiene, and styrene, polyurethanes, polyurethanes, polyesters, polyolefins, and polyamides.

The compounds of formula (I) and (II) may be incorporated in the polymeric material by any of the various procedures known in the art for such purpose, such as by dry blending the stabilizer with the polymer in powder or granular form followed by milling, Banbury mixing, molding, casting, extruding, swelling, and the like; by immersing the polymer as film, sheet, fibers, etc. in a solution of the stabilizer in an appropriate solvent (as in a dyeing process), etc.

The amount of the compound of formula (I) or (II) which is incorporated into the polymeric material in order to achieve effective protection against degradation by actinic radiation, varies according to the properties of the polymeric material treated and according to the severity of the actinic radiation and of the length of exposure. However, for most purposes, it is sufficient to use an amount of the compound of formula (I) or (II), within the range of from 0.01 percent to about 3 percent by weight, preferably within the range of about 0.05 percent to 1 percent by weight based on the weight of untreated polymeric material.

Optionally, the composition of the invention may contain further additives, especially those used in polyolefin formulations, such as antioxidants, other light or UV stabiliziers, pigments, anti-slipping and anti-static agents, fillers and dyes.

Examples of suitable antioxidants are those of the hindered phenol type such as 2,6-di-tertiarybutyl-p-cresol, 4,4'-bis(2,6-di-tert.-butylphenol), 4,4'-bis(2,6-diisopropylphenol), 2,4,6-tri-tert.-butylphenol, 2,2'-thio-bis(4-methyl-6-tertiarybutyl-phenol), octadecyl 2[3'5'-di-tert.-butyl-4'-hydroxyphenyl]propionate and esters of thiodipropionic acid, for example dilauryl thiodipropionate; alkyl, aryl or alkaryl phosphites such as triphenyl phosphite, trinonyl phosphite and diphenyldecyl phosphite; and combinations of these antioxidants.

Supplemental light stabilizers include those of the substituted benzotriazole class such as 2-(2'-hydroxy-5'-methylphenyl)benzotriazole, 2-(2'-hydroxy-2',5'-di-tert.-butylphenyl)-5-chlorobenzotriazole; those of the hydroxybenzophenone type; hindered phenols such as 2',4'-di-tert.-butylphenyl-3,5-di-tert.-butyl-4-hydroxybenzoate, and suitable metal complexes; for example, nickel complexes of 2,2'-thiobis-(4-tertiary octylphenol), such as the 1:1 and 1:2 complex, optionally with other ligands such as n-butylamine; nickel complexes of bis-(4-tertiary octylphenyl) sulphone such as the 2:1 complex; nickel dibutyl dithiocarbamate; nickel salts of 4-hydroxy-3,5-di-tertiary butylbenzyl phosphonic acid mono alkyl esters, such as the methyl-, ethyl- or butyl esters; and the nickel complex of 2-hydroxy-4-methyl-phenyl-undecyl ketone oxime.

As with the compounds of formulas (I) and (II), any further additive may advantageously be employed in a proportion within the range of from about 0.05 percent to 1 percent by weight, based on the weight of untreated organic material.

In combination with an antioxidant suitable for use in inhibiting oxidative deterioration of polyolefins, for instance those of the hindered phenol type, the compounds of formulas (I) and (II) provide extremely effective all-around stabilizers for polyolefins, especially polypropylene.

The following examples further illustrate the present invention. Parts and percentages shown therein are by weight unless otherwise stated.

EXAMPLE 1

Preparation of
2,2,3,3-Tetramethyl-1,4-Diazaspiro[4.5]decane

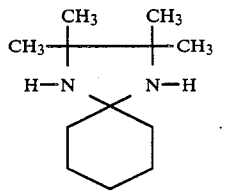

2,3-Diamino-2,3-dimethylbutane dihydrochloride is neutralized with aqueous caustic soda and the diamine is recovered. The wet diamine (15.3 grams) is then heated with benzene (150 mls) to azeotrope off about 2.2 mls of water. The benzene, containing 13.1 grams (0.113 mole) of the diamine, is then treated with cyclohexanone (11.0 grams 0.112 mole) and p-toluenesulfonic acid (50 mgs) and the reaction mixture is refluxed for 40 hours in a flask fitted with a Dean-Stark water separator. The benzene is then removed by distillation and the reddish liquid residue is fractionally distilled. The main fraction, b.p 82°–84° C. at 1 mm pressure, has a nuclear magnetic resonance spectrum identical to that reported in the literature [Keana et al., J. Am. Chem. Soc. 100, pg. 934 (1978)]. On standing the liquid solidifies to a crystalline solid, m.p. 31°–32° C., which contains 9.95% water.

EXAMPLES 2-9

In the manner described in Example 1, utilizing 2,3-diamino-2,3-dimethylbutane dihydrochloride and the appropriate ketone, the following compounds are prepared:

| | COMPOUND | |
|---|---|---|
| Example | Structure | Name |
| 2 | (structure with C$_9$H$_{19}$ substituent) | 2,2,3,3-tetramethyl-8-nonyl-1,4-diazaspiro[4.5]decane |
| 3 | (structure with OC$_4$H$_9$ substituent) | 7-butoxy-2,2,3,3-tetramethyl-1,4-diazaspiro[4.5]decane |
| 4 | (structure with CH$_2$C(O)—OC$_{16}$H$_{33}$ substituent) | 7-[[(hexadecyloxy)carbonyl]-methyl]-2,2,3,3-tetramethyl-1,4-diazaspiro[4.5]decane |

-continued

| Example | Structure | Name |
|---|---|---|
| 5 | CH₃–C(CH₃)(NH)—C(CH₃)(NH)—[cyclohexane with SC₁₂H₂₅] | 7-dodecylthio-2,2,3,3-tetramethyl-1,4-diazaspiro[4.5]decane |
| 6 | CH₃–C(CH₃)(NH)—C(CH₃)(NH)—[cyclohexane with (CH₂CH₂CN)₂ at two positions] | 6,6,10,10-tetrakis(2-cyanoethyl)-2,2,3,3-tetramethyl-1,4-diazaspiro[4.5]decane |
| 7 | CH₃–C(CH₃)(NH)—C(CH₃)(NH)—C(CH₃)((CH₂)₅CH₃) | 2-hexyl-2,4,4,5,5-pentamethylimidazolidine |
| 8 | Two pentamethylimidazolidine units linked via CH₂—CH₂ bridge | 2,2'-ethylenebis(2,4,4,5,5-pentamethylimidazolidine) |
| 9 | CH₃–C(CH₃)(NH)—C(CH₃)(NH)—[cyclohexane with CH₂C(O)OC₂H₅] | 7[[(ethyloxy)carbonyl]methyl]-2,2,3,3-tetramethyl-1,4-diazaspiro[4.5]decane |

EXAMPLE 10

7,7'-[Hexamethylenebis(oxycarbonylmethyl)-]Bis(2,2,3,3-Tetramethyl-1,4-diazaspiro[4.5]decane)

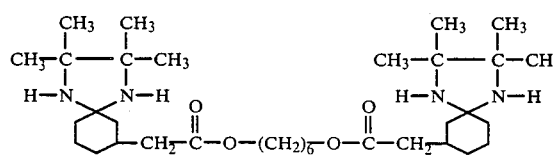

The above compound is prepared by transesterification utilizing the compound of Example 9 and 1,3-hexanediol as the reactants.

EXAMPLE 11

1,2,2,3,3,4-Hexamethyl-1,4-Diazaspiro[4.5]decane

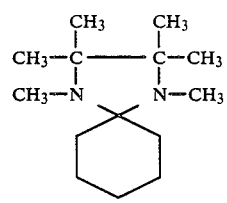

The above compound is prepared by slurrying one molecular proportion of the compound of Example 1 in water with 2 molecular proportions of formaldehyde, as a 37% solution, and adding dropwise 6 molecular proportions of formic acid, as an 88% solution. After the addition is completed, the reaction mixture is refluxed overnight and then cooled to room temperature. The pH of the reaction mixture is then adjusted to 11.5 by adding aqueous caustic soda and the reaction mixture is extracted with methylene chloride. The organic phase is separated and the solvent is evaporated to obtain the desired product.

EXAMPLE 12

Evaluation of Light Stabilization Properties

The resistance to degradation by ultraviolet light is determined by dry-blending and milling 0.5 part of the additive under test, 100 parts of unstabilized polypropylene and 0.1 part of 2,4,6-tri-tert.-butylphenol, a processing antioxidant, on a standard two-roll mill at 350°–370° F. for 4–5 minutes and compression molding the milled composition at 400° F. into films 4–5 mils thick. The film is then exposed in a carbon arc Atlas Fade-Ometer ®, (Atlas Electric Devices Co., Chicago, Ill.), hereafter abbreviated FOM, and in a xenon arc Atlas Weather-Ometer ®, hereafter abbreviated WOM, without using a water spray, until the carbonyl content of the film increases by 0.10% by weight, as determined by infrared spectrophotometric measurement. A control film identically prepared, without the additive under test, is similarly prepared and tested. The time in hours required to increase the carbonyl content of the film by 0.1% coincides with the time required to reach the point of embrittlement.

The results obtained are shown in Table I.

TABLE I

| Example | Product of Example | Time (Hr.) to Increase Carbonyl Content 0.10% | |
|---|---|---|---|
| | | FOM | WOM |
| 12 | 1 | 700 | 2000 |
| | Control[a] | 300–500 | 800–1000 |

[a]The control sample consisted of unstabilized polypropylene containing 0.1% by weight of 2,4,6-tri-tert.-butylphenol.

These results show that the compound of Example 1 is effective in prolonging the resistance to polypropylene to degradation by ultraviolet radiation.

In the manner described above, substituting the compounds of Examples 2–11 for the compound of Example 1, similar results are obtained.

What is claimed is:

1. A compound of the formula:

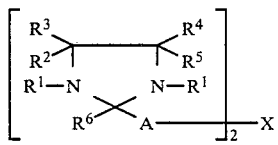

wherein;
(1) $R^1$ represents hydrogen, alkyl ($C_1$–$C_6$) hydroxyl, or oxyl;
(2) $R^2$ and $R^3$, which may be the same or different, represent alkyl ($C_1$–$C_6$), cycloalkyl ($C_5$–$C_6$), or together with the carbon to which they are attached form a cycloalkyl ($C_5$–$C_6$) radical;
(3) $R^4$ and $R^5$, which may be the same or different, represent the same groups as $R^2$ and $R^3$;
(4) $R^6$ represents:
 (a) alkyl ($C_1$–$C_{18}$); or
 (b) substituted alkyl ($C_1$–$C_8$); or
 (c) together with the carbon to which are attached form a cycloalkyl ($C_5$–$C_6$) radical; or
 (d) optionally, (C) is substituted with alkyl ($C_1$–$C_8$); or
 (e) substituted cycloalkyl ($C_5$–$C_6$) radical; or
 (f) a substituted alkyl ($C_1$–$C_8$) - substituted cycloalkyl ($C_5$–$C_6$) radical;

wherein said substitutents of (b), (e) and (f) are selected from:
 (i) amino; or
 (ii) cyano; or
 (iii) hydroxy; or
 (iv)

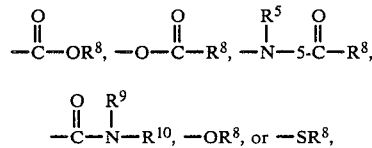

wherein $R^8$ is selected from alkyl ($C_1$–$C_{18}$) and cycloalkyl ($C_5$–$C_6$), $R^9$ is hydrogen, alkyl ($C_1$–$C_{18}$), or cycloalkyl ($C_5$–$C_6$), $R^{10}$ is alkyl ($C_1$–$C_{18}$) or cycloalkyl ($C_5$–$C_6$), or $R^9$ and $R^{10}$, together with the nitrogen atom to which they are attached, form a ring represented by the formula:

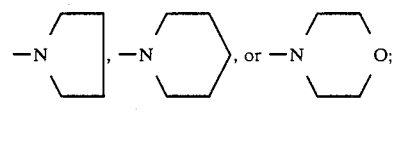

or
 (v)

wherein $R^9$ and $R^{10}$ are as defined in (iv);
(5) the group

represents:
 (a) alkylene ($C_2$–$C_6$); or
 (b) arylene ($C_6$–$C_{10}$); or
 (c) arylenedialkyl ($C_8$–$C_{12}$); or
 (d) a substituted alkylene ($C_1$–$C_8$); or
 (e) A together with $R^6$ and the carbon atom to which they are attached form a substituted cycloalkyl ring ($C_5$–$C_6$);
wherein the substituents of (d) and (e) are:

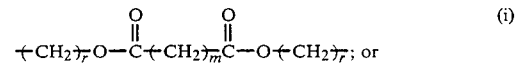

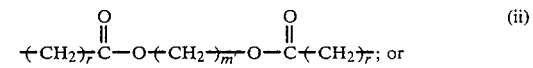

wherein m is zero to 6, m' is 2 to 6, and r is zero to 2.

2. A method of stabilizing a polymer which is normally subject to degradation by ultraviolet radiation which comprises incorporating into said polymer an ultraviolet radiation stabilizingly effective amount of a stabilizer compound of the formula:

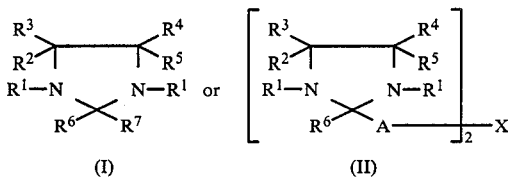

wherein:
(1) $R^1$ represents hydrogen, alkyl ($C_1$-$C_6$) hydroxyl, or oxyl;
(2) $R^2$ and $R^3$, which may be the same or different, represent alkyl ($C_1$-$C_6$), cycloalkyl ($C_5$-$C_6$), or together with the carbon to which they are attached form a cycloalkyl ($C_5$-$C_6$) radical;
(3) $R^4$ and $R^5$, which may be the same or different, represent the same groups as $R^2$ and $R^3$;
(4) $R^6$ and $R^7$, which may be the same or different represent;
  (a) alkyl ($C_1$-$C_{18}$); or
  (b) substituted alkyl ($C_1$-$C_8$); or
  (c) together with the carbon to which they are attached form a cycloalkyl ($C_5$-$C_6$) radical; or
  (d) optionally, (C) is substituted with alkyl ($C_1$-$C_8$); or
  (e) substituted cycloalkyl ($C_5$-$C_6$) radical; or
  (f) a substituted alkyl ($C_1$-$C_8$) - substituted cycloalkyl ($C_5$-$C_6$) radical;
wherein said substitutents of (b), (e) and (f) are selected from:
  (i) amino; or
  (ii) cyano; or
  (iii) hydroxy; or
  (iv)

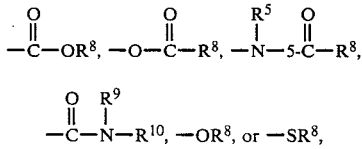

wherein $R^8$ is selected from alkyl ($C_1$-$C_{18}$) and cycloalkyl ($C_5$-$C_6$), $R^9$ is hydrogen, alkyl ($C_1$-$C_{18}$), or cycloalkyl ($C_5$-$C_6$), $R^{10}$ is alkyl ($C_1$-$C_{18}$) or cycloalkyl ($C_5$-$C_6$), or $R^9$ and $R^{10}$, together with the nitrogen atom to which they are attached, form a ring represented by the formula:

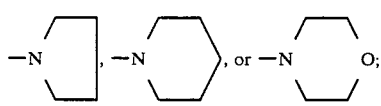

or
(v)

wherein $R^9$ and $R^{10}$ are as defined in (iv);
(5) the group

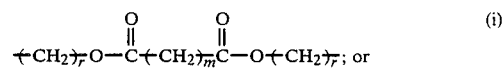

represents:
(a) alkylene ($C_2$-$C_6$); or
(b) arylene ($C_6$-$C_{10}$); or
(c) arylenedialkyl ($C_8$-$C_{12}$); or
(d) a substituted alkylene ($C_1$-$C_8$); or
(e) A together with $R^6$ and the carbon atom to which they are attached form a substituted cycloalkyl ring ($C_5$-$C_6$);
wherein the substituents of (d) and (e) are:

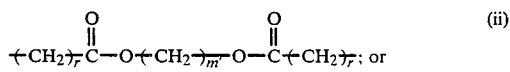

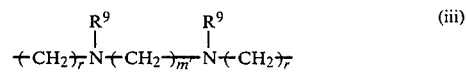

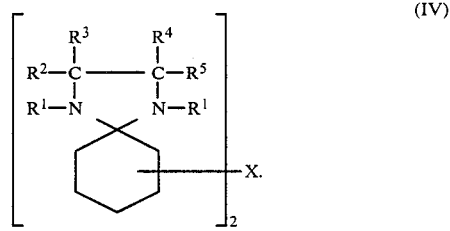

wherein m is zero to 6, m' is 2 to 6, and r is zero to 2.

3. A compound according to Claim 1 of the formula:

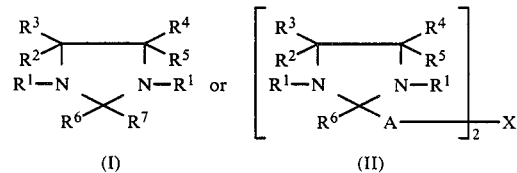

4. A composition comprising a polymer which is normally subject to degradation by ultraviolet radiation and an ultraviolet radiation stabilizingly effective amount of a stabilizer compound of the formula:

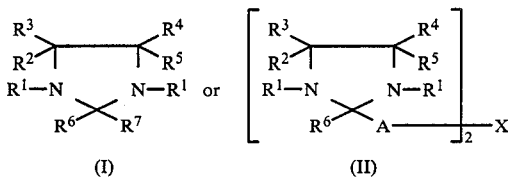

wherein:
(1) $R^1$ represents hydrogen, alkyl ($C_1$-$C_6$) hydroxyl, or oxyl;
(2) $R^2$ and $R^3$, which may be the same or different, represent alkyl ($C_1$-$C_6$), cycloalkyl ($C_5$-$C_6$), or together with the carbon to which they are attached form a cycloalkyl ($C_5$-$C_6$) radical;
(3) $R^4$ and $R^5$, which may be the same or different, represent the same groups as $R^2$ and $R^3$;
(4) $R^6$ and $R^7$, which may be the same or different, represent:
  (a) alkyl ($C_1$-$C_{18}$); or
  (b) substituted alkyl ($C_1$-$C_8$); or (c) together with the carbon to which they are attached form a cycloalkyl (C$_5$–C$_6$) radical; or
(d) optionally, (C) is substituted with alkyl (C$_1$–C$_8$); or
(e) substituted cycloalkyl (C$_5$–C$_6$) radical; or
(f) a substituted alkyl (C$_1$–C$_8$) - substituted cycloalkyl (C$_5$–C$_6$) radical;
wherein said substitutents of (b), (e) and (f) are selected from:
(i) amino; or
(ii) cyano; or
(iii) hydroxy; or
(iv)

$$-\overset{O}{\underset{\|}{C}}-OR^8, \quad -O-\overset{O}{\underset{\|}{C}}-R^8, \quad -\underset{|}{N}-5-\overset{O}{\underset{\|}{C}}-R^8,$$

$$-\overset{O}{\underset{\|}{C}}-\underset{|}{\overset{R^9}{N}}-R^{10}, \quad -OR^8, \text{ or } -SR^8,$$

wherein $R^8$ is selected from alkyl (C$_1$–C$_{18}$) and cycloalkyl (C$_5$–C$_6$), $R^9$ is hydrogen, alkyl (C$_1$–C$_{18}$), or cycloalkyl (C$_5$–C$_6$), $R^{10}$ is alkyl (C$_1$–C$_{18}$) or cycloalkyl (C$_5$–C$_6$), or $R^9$ and $R^{10}$, together with the nitrogen atom to which they are attached, form a ring represented by the formula:

$$-N\diagdown\diagup, \quad -N\diagdown\diagup, \text{ or } -N\diagdown\diagup O;$$

or
(v)

$$-N\diagdown\overset{R^9}{\diagdown}_{R^{10}}$$

wherein $R^9$ and $R^{10}$ are as defined in (iv);
(5) the group $$\uparrow A \uparrow_{\overline{2}} X$$

represents:
(a) alkylene (C$_2$–C$_6$); or
(b) arylene (C$_6$–C$_{10}$); or
(c) arylenedialkyl (C$_8$–C$_{12}$); or
(d) a substituted alkylene (C$_1$–C$_8$); or
(e) A together with $R^6$ and the carbon atom to which they are attached form a substituted cycloalkyl ring (C$_5$–C$_6$);
wherein the substituents of (d) and (e) are:

$$+CH_2\frac{}{r}O-\overset{O}{\underset{\|}{C}}+CH_2\frac{}{m}\overset{O}{\underset{\|}{C}}-O+CH_2\frac{}{r}; \text{ or } \quad (i)$$

$$+CH_2\frac{}{r}\overset{O}{\underset{\|}{C}}-O+CH_2\frac{}{m}O-\overset{O}{\underset{\|}{C}}+CH_2\frac{}{r}; \text{ or } \quad (ii)$$

$$+CH_2\frac{}{r}\underset{|}{\overset{R^9}{N}}+CH_2\frac{}{m'}\underset{|}{\overset{R^9}{N}}+CH_2\frac{}{r} \quad (iii)$$

wherein m is zero to 6, m' is 2 to 6, and r is zero to 2.

5. A compound according to claim 3 wherein $R^1$ is hydrogen and $R^2$–$R^5$ are each methyl.

6. The method of claim 2 wherein the stabilizer is incorporated in a concentration of from about 0.01 to about 3% based on the weight of the polymer.

7. The method of claim 6 wherein the polymer is a polyolefin.

8. The method of claim 7 wherein the polyolefin is polypropylene.

9. A method according to claim 2 wherein said stabilizer has the formula:

$$\text{(III)}$$

wherein $X^1$ represents hydrogen, C$_1$–C$_{18}$ alkyl, or a member selected from the substituents for $R^6$ and $R^7$.

10. A method according to claim 2 wherein said stabilizer has the formula:

$$\text{(IV)}$$

11. A compound according to claim 9 wherein $R^1$ is hydrogen and $R^2$–$R^5$ are each methyl.

12. A compound according to claim 10 wherein $R^1$ is hydrogen and $R^2$–$R^5$ are each methyl.

13. A compound according to claim 11 wherein $X^1$ is hydrogen.

14. The composition of claim 4 wherein the stabilizer is incorporated in a concentration of from about 0.01 to about 3% based on the weight of the polymer.

15. The composition of claim 14 wherein the polymer is a polyolefin.

16. The method of claim 15 wherein the polyolefin is polypropylene.

17. A composition according to claim 4 wherein said stabilizer compound has the formula $$\text{(III)}$$

wherein $X^1$ represents hydrogen, $C_1$–$C_{18}$ alkyl, or a member selected from the substituents for $R^6$ and $R^7$.

18. A composition according to claim 4 wherein said stabilizer compound has the formula:

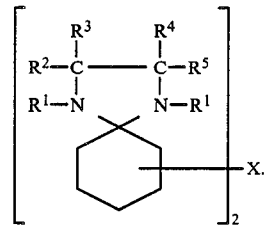

(IV)

19. A composition according to claim 17 wherein $R^1$ is hydrogen and $R^2$–$R^5$ are each methyl.

20. A composition according to claim 18 wherein $R^1$ is hydrogen and $R^2$–$R^5$ are each methyl.

21. A composition according to claim 19 wherein $X^1$ is hydrogen.

* * * * *